United States Patent [19]

Lesher et al.

[11] Patent Number: 4,599,423
[45] Date of Patent: Jul. 8, 1986

[54] PREPARATION OF 5-(HYDROXY- AND/OR AMINOPHENYL-6-LOWER-ALKYL)-2(1H)-PYRIDINONES

[75] Inventors: George Y. Lesher; Chester J. Opalka, Jr., both of Schodack; Donald F. Page, East Greenbush; Ruthann M. McGarry, Schodack, all of N.Y.

[73] Assignee: Sterling Drug Inc., New York, N.Y.

[21] Appl. No.: 595,751

[22] Filed: Apr. 2, 1984

Related U.S. Application Data

[60] Division of Ser. No. 372,174, Apr. 26, 1982, Pat. No. 4,465,686, which is a continuation-in-part of Ser. No. 300,294, Sep. 8, 1981, abandoned.

[51] Int. Cl.$^4$ ............................................. C07D 211/76
[52] U.S. Cl. ................................... 546/300; 546/301; 546/288
[58] Field of Search ................................. 546/300, 301

[56] References Cited

U.S. PATENT DOCUMENTS

| | | | |
|---|---|---|---|
| 3,655,679 | 4/1972 | Shen et al. | 546/298 |
| 3,703,582 | 11/1972 | Shen et al. | 514/354 |
| 3,718,743 | 2/1973 | Shen et al. | 514/327 |
| 4,004,012 | 1/1977 | Lesher et al. | 514/334 |
| 4,072,746 | 2/1978 | Lesher et al. | 514/334 |
| 4,276,293 | 6/1981 | Lesher et al. | 514/300 |
| 4,297,362 | 10/1981 | Lesher et al. | 514/357 |
| 4,302,462 | 11/1981 | Collins et al. | 514/277 |
| 4,312,875 | 1/1982 | Lesher et al. | 514/334 |
| 4,313,951 | 2/1982 | Lesher et al. | 514/334 |

OTHER PUBLICATIONS

Julia et al., Bull. Soc. Chim. (France), 2387–2394 (1966).

*Primary Examiner*—Alan L. Rotman
*Attorney, Agent, or Firm*—Robert K. Bair; Paul E. Dupont; B. Woodrow Wyatt

[57] ABSTRACT

Disclosed and claimed is the cardiotonic use of 1-$R_1$-5-(3-R'-4-R''-phenyl)-6-R-2(1H)-pyridinones (II), where $R_1$ is hydrogen, lower-alkyl or lower-hydroxyalkyl, R is lower-alkyl or hydrogen, and, R' and R'' are each hydrogen, amino or hydroxy, at least one of R' or R'' being other than hydrogen, or where R' is nitro when R'' is hydroxy, or pharmaceutically acceptable acid-addition salts thereof where at least one of R' and R'' is amino. Also disclosed and claimed are 1-$R_1$-5-(3-R'-4-R''-phenyl)-6-R-2(1H)-pyridinones (I), where $R_1$, R' and R'' are defined as above and R is lower-alkyl and acid-addition salts thereof where at least one of R' and R'' is amino. Also shown and claimed is the process which comprises reacting 1-$R_1$-1,2-dihydro-2-oxo-5-(3-R'-4-R''-phenyl)-6-R-nicotinonitrile, where $R_1$ and R are defined as above for II, R' is hydrogen, hydroxy, methoxy or amino and R'' is hydroxy, methoxy or hydrogen, preferably at least one of R' and R'' being methoxy, or where R' is nitro and R'' is hydrogen or methoxy, preferably methoxy, with 85% phosphoric acid to produce 1-$R_1$-5-(3-R'-4-R''-phenyl)-6-R-2(1H)-pyridinone, where $R_1$ and R are defined as above for II, R' is hydrogen, hydroxy or amino and R'' is hydroxy or hydrogen, at least one of R' and R'' being hydroxy, or where R' is nitro and R'' is hydroxy.

8 Claims, No Drawings

PREPARATION OF 5-(HYDROXY- AND/OR AMINOPHENYL-6-LOWER-ALKYL)-2(1H)-PYRIDINONES

CROSS-REFERENCE TO RELATED APPLICATIONS

This application is a division of copending U.S. patent appplication Ser. No. 372,174, filed Apr. 26, 1982, now U.S. Pat. No. 4,465,686, issued Aug. 14, 1984, which in turn is a continuation-in-part of copending U.S. patent application Ser. No. 300,294, filed Sept. 8, 1981 and now abandoned.

The 1-$R_1$-1,2-dihydro-2-oxo-5-(substituted-phenyl)-6-R-nicotinonitriles, used herein as intermediates, are disclosed as cardiotonic agents and as intermediates for preparing the corresponding 3-amino-1-$R_1$-5-(substituted-phenyl)-6-R-2(1H)-pyridinones and are claimed in copending Lesher, Opalka and Page U.S. patent application Ser. No. 355,229, filed Mar. 5, 1982, now U.S. Pat. No. 4,515,797, issued May 7, 1985 as a continuation-in-part of its copending U.S. patent applications Ser. No's. 300,294, filed Sept. 8, 1981 and now abandoned and 348,450, filed Feb. 12, 1982 and now abandoned, the latter as a continuation-in-part of its copending U.S. patent application Ser. No. 248,840, filed Mar. 30, 1981 and now abandoned.

BACKGROUND OF THE INVENTION (a) Field of the Invention

This invention relates to 5-(substituted-phenyl)-2(1H)-pyridinones, their preparation and their use as cardiotonics.

(b) Description of the Prior Art

Julia et al., Bull. soc. chim. (France), 2387–2394 (1966), show inter alia the reaction of 1-hydroxymethylene-1-phenyl-2-propanone with α-cyanoacetamide to produce 2-hydroxy-5-(unsubstituted-phenyl)-6-methylnicotinonitrile and the reaction of 3-dimethylamino-2-phenyl-2-propenal (same as β-dimethylamino-α-phenylacrolein) with α-cyanoacetamide to produce 2-hydroxy-5-(unsubstituted-phenyl)nicotinonitrile. These 2-hydroxy compounds, tautomers of the corresponding 1,2-dihydro-2(1H)-pyridinones, were converted to their corresponding carboxylic acids and ethyl or methyl esters and also to their 2-chloro compounds and 5-(unsubstituted-phenyl)-3-piperidinecarboxamide derivatives, representative members of which were found to have pharmacological activity resembling that of lysergamide.

Shen et al. U.S. Pat. No. 3,718,743, issued Feb. 27, 1973, shows "5-phenyl-2-piperidinones and 5-phenyl-2-thiopiperidinones in compositions and methods for treating pain, fever and inflammation". The generic teaching of these piperidinones shows that "phenyl" can have one or two substituents at positions 2, 3, 4, 5 and/or 6, e.g., inter alia, nitro, amino, lower-alkyl, lower alkylamino and lower-alkylmercapto. Various means of preparing the 5-phenyl-2-piperidinone final products are shown. In one procedure, a 2-chloro-5-phenylpyridine was heated with aqueous sodium hydroxide in dimethylformamide to produce the corresponding 5-phenyl-2(1H)-pyridinones which were then hydrogenated to produce the desired 5-phenyl-2-piperidinones. Among the 5-phenyl-2(1H)-pyridinones specifically shown is 5-(4-hydroxyphenyl)-2(1H)-pyridinone and its preparation by heating the corresponding 5-(4-methoxyphenyl)-2(1H)-pyridinone with pyridine hydrochloride under nitrogen. The only use shown for said 5-(4-hyroxyphenyl)2(1H)-pyridinone is as an intermediate.

Shen et al U.S. Pat. Nos. 3,655,679, issued Apr. 11, 1972, and 3,703,582, issued Nov. 21, 1972, show as antiinflammatory, analgesic and antipyretic agents various aryl-hydroxy-pyridinecarboxylic acids and lower-alkyl esters thereof, among which are 5-(substituted-phenyl)-2-hydroxynicotinic acid. These latter compounds were prepared by reacting a 2-(substituted-phenyl)-3-dimethylamino-2-propenal with cyanoacetamide to first produce 5-(substituted-phenyl)-2-hydroxynicotinonitrile, illustrated inter alia by the compounds where substituted-phenyl is 4-chlorophenyl, 3,4-dihydroxyphenyl, 4-nitrophenyl, 4-benzoylaminophenyl and 2,6-dimethoxyphenyl. Also shown is the preparation of the corresponding 2-hydroxy-6-methyl-5-(substituted-phenyl)-nicotinonitrile by reacting 2-(substituted-phenyl)-acetoacetaldehyde with cyanoacetamide followed by hydrolysis of the nicotinonitrile to the corresponding nicotinic acid. Illustrations of intermediate nicotinonitriles produced by this procedure include inter alia the compounds where substituted-phenyl is 2-hydroxyphenyl, 4-methoxyphenyl and 4-aminophenyl.

Lesher and Opalka [U.S. Pat. Nos. 4,004,012, issued Jan. 18, 1977, and 4,072,746, issued Feb. 7, 1978]show as cardiotonic agents 3-amino(or cyano)-5-(pyridinyl)-2(1H)-pyridinones. A preferred embodiment of these compounds is 3-amino-5-(4-pyridinyl)-2(1H)-pyridinone, now generically known as amrinone and alternatively named 5-amino-[3,4'-bipyridin]-6(1H)-one. One method shown for preparing the 3-cyano-5-(pyridinyl)-2(1H)-pyridinones, alternatively named 1,2-dihydro-2-oxo-5-(pyridinyl)nicotinonitriles, is the reaction of α-(pyridinyl)-β-(dialkylamino)acrolein with α-cyanoacetamide. U.S. Pat. No. 4,072,746 also shows inter alia, 3-Q-5-(pyridinyl)-2(1H)-pyridinones where Q is hydrogen. The disclosure of U.S. Pat. No. 4,072,746 also is shown in Lesher and Opalka U.S. Pat. Nos. 4,107,315, 4,137,233, 4,199,586 and 4,225,715.

Lesher, Opalka and Page U.S. Pat. No. 4,276,293, issued June 30, 1981, shows inter alia 1,2-dihydro-6-(lower-alkyl)-2-oxo-5-(pyridinyl)nicotinonitriles by reacting a 1-(pyridinyl)-2-(dimethylamino)ethenyl lower-alkyl ketone with α-cyanoacetamide and the conversion, by hydrolysis and decarboxylation, of said nicotinonitriles to the corresponding 6-(lower-alkyl)-5-(pyridinyl)-2(1H-pyridinones.

Lesher and Philion pending U.S. patent application Ser. No. 198,461, filed Oct. 20, 1980 and now U.S. Pat. No. 4,313,951, issued Feb. 2, 1982, a continuation-in-part of application Ser. No. 97,504, filed Nov. 26, 1979 and now abandoned, discloses and claims as cardiotonics, inter alia, 1,2-dihydro-6-(lower-alkyl)-2-oxo-5-(pyridinyl)nicotinonitriles and their preparation.

Lesher, Opalka and Page U.S. patent application Ser. No. 204,726, filed Nov. 6, 1980 and now U.S. Pat. No. 4,312,875, issued Jan. 26, 1982, a continuation-in-part of U.S. application Ser. No. 135,100, filed Mar. 28, 1980 and now U.S. Pat. No. 4,297,360, issued Oct. 27, 1981, discloses and claims as cardiotonics, 6-(lower-alkyl)-5-(pyridinyl)-2(1H)-pyridinones.

Lesher and Singh U.S. Pat. No. 4,297,362, issued Oct. 27, 1981, shows 4-(3,4-diaminophenyl)pyridine or salt and its cardiotonic use.

Collins, Lesher and Singh U.S. Pat. No. 4,302,462, issued Nov. 24, 1981, shows 4-(4- or 3-pyridinyl)-1,2-benzenediol or salt and dimethyl ethers thereof as cardiotonic agents.

(c) Prior Publications

Alousi et al, Fed. Proc., Pt. I, Abstracts, item 2478, page 663, Mar. 1, 1981 (65th Annual Meeting, Atlanta, Ga., Apr. 12–17, 1981), show 1,2-dihydro-6-methyl-2-oxo-5-(4-pyridinyl)nicotinonitrile, also named 1,6-dihydro-2-methyl-6-oxo-[3,4'-bipyridine]-5-carbonitrile, to be more active than amrinone, namely, 3-amino-5-(4-pyridinyl)-2(1H)-pyridinone.

The following publications appeared prior to the filing of the instant application but subsequent the filing of parent application Ser. No. 300,294 and subsequent to completion of applicants' invention disclosed and claimed herein: Sandoz AG Patent Cooperation Treaty Application No. 81/02575, published Sept. 17, 1981, and corresponding U.K. Patent Applications No. 2,070,606, published Sept. 9, 1981, which disclose, inter alia, as cardiotonic agents and claim selected 3-amino-6-$R_2$-5-aryl-2(1H)-pyridinones where $R_2$ is hydrogen or lower-alkyl and aryl is, inter alia, phenyl, 4-methoxyphenyl, 3-methoxyphenyl or 3,4-dimethoxyphenyl. These compounds are reportedly prepared from the corresponding 1,2-dihydro-2-oxo-6-$R_2$-5-arylnicotinamides, in turn, prepared from the corresponding 1,2-dihydro-2-oxo-6-$R_2$-5-arylnicotinonitriles.

SUMMARY OF THE INVENTION

In a composition of matter aspect, the invention resides in 1-$R_1$-5-[3- and/or 4-(hydroxy and/or amino)phenyl or 4-hydroxy-3-nitrophenyl]-6-(lower-alkyl)-2(1H)-pyridinones (I) and salts, useful as cardiotonic agents, where $R_1$ is hydrogen, lower-alkyl or lower-hydroxyalkyl.

A composition aspect of the invention resides in the cardiotonic composition for increasing cardiac contractility, said composition comprising a pharmaceutically acceptable carrier, and as the active component thereof, a cardiotonically-effective amount of 1-$R_1$-5-[3-and/or 4-(hydroxy and/or amino)phenyl or 4-hydroxy-3-nitrophenyl]-6-R-2(1H)-pyridinone (II) or salt thereof, where $R_1$ is defined as above and R is hydrogen or lower-alkyl.

A method aspect of the invention resides in the method for increasing cardiac contractility in a patient requiring such treatment which comprises administering a medicament comprising a pharmaceutically acceptable carrier and, as the active component, a cardiotonically effective amount of 1-$R_1$-5-[3- and/or 4-(hydroxy and/or amino)phenyl or 4-hydroxy-3-nitrophenyl]-6-R-2(1H)-pyridinone (II) or salt thereof, where R and $R_1$ are defined as above.

In a process aspect the invention resides in the process for preparing 1-$R_1$-5-(3-R'-4-R''-phenyl)-6-R-2(1H)-pyridinone, where $R_1$ and R are defined as above, R' is hydrogen, hydroxy or amino and R'' is hydroxy or hydrogen or where R' is nitro when R'' is hydroxy, at least one of R' and R'' being hydroxy, which comprises reacting a 1-$R_1$-1,2-dihydro-2-oxo-5-(3-R'-4-R''-phenyl)-6-R-nicotinonitrile, where $R_1$ and R are defined as above, R' is hydrogen, hydroxy, methoxy or amino and R'' is hydroxy, methoxy or hydrogen, preferably at least one of R' and R'' being methoxy, or where R' is nitro when R'' is hydroxy or methoxy, preferably methoxy, with 85% phosphoric acid.

DETAILED DESCRIPTION INCLUSIVE OF PREFERRED EMBODIMENTS

A composition of matter aspect of the invention resides in a 1-$R_1$-5-(3-R'-4-R''-phenyl)-6-R-2(1H)-pyridinone having formula I

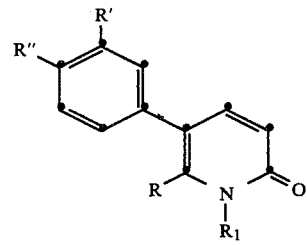

where $R_1$ is hydrogen, lower-alkyl or lower-hydroxyalkyl, R is lower-alkyl, R' and R'' are each hydrogen, amino or hydroxy, at least one of R' or R'' being other than hydrogen, or where R' is nitro and R'' is hydroxy; or an acid-addition salt thereof where at least one of R' and R'' is amino. The compounds of formula I are useful as cardiotonics, as determined by standard pharmacological evaluation procedures. Preferred embodiments are those of formula I where $R_1$ is hydrogen, R is methyl or ethyl, R' is hydrogen, hydroxy or amino and R'' is hydroxy or hydrogen, the latter only when R' is other than hydrogen. Particularly preferred embodiments are the compounds of formula I where R is methyl, $R_1$ is hydrogen, and one of or both R'' and R' represent hydroxy or R' is amino and R'' is hydroxy.

A composition aspect of the invention resides in a cardiotonic composition for increasing cardiac contractility, said composition comprising a pharmaceutically acceptable carrier and, as the active component thereof, a cardiotonically effective amount of 1-$R_1$-5-(3-R'-4-R''-phenyl)-6-R-2(1H)-pyridinone having formula II

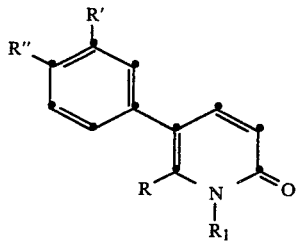

II where $R_1$, R' and R" have the above-given definitions of formula I and R is hydrogen or lower-alkyl; or pharmaceutically acceptable acid-addition salt thereof where at least one of R' and R" is amino. Preferred embodiments of this composition aspect of the invention are those where the active component is the compound of formula II where $R_1$ is hydrogen, R is hydrogen, methyl or ethyl, R' is hydrogen, hydroxy or amino, and R" is hydroxy or hydrogen the latter only when R' is other than hydrogen. Particularly preferred embodiments are those where the active component is the compound of formula II where R is methyl, $R_1$ is hydrogen and one or both R" and R' represent hydroxy or R' is amino and R" is hydroxy.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of 1-$R_1$-5-(3-R'-4-R"-phenyl)-6-R-2(1H)-pyridinone of formula II hereinabove where $R_1$, R' and R" have the previously given meanings and R is hydrogen or lower-alkyl; or pharmaceutically acceptable salt thereof where at least one of R' and R" is amino. Preferred and particularly preferred embodiments of this method aspect of the invention are those where the active component is the same as the active component of the respective preferred and particularly preferred composition embodiments described in the immediately preceding paragraph.

A process aspect of the invention resides in the process which comprises reacting a 1-$R_1$-1,2-dihydro-2-oxo-5-(3-R'-4-R"-phenyl)-6-R-nicotinonitrile, where $R_1$ and R are defined as in formula II, R' is hydrogen, hydroxy, methoxy or amino and R" is hydroxy, methoxy or hydrogen, preferably at least one of R' and R" being methoxy, or where R' is nitro when R" is hydroxy or methoxy, preferably methoxy, with 85% phosphoric acid to produce 1-$R_1$-5-(3-R'-4-R"-phenyl)-6-R-2(1H)-pyridinone, where $R_1$ and R have the meanings given above, R' is hydrogen, hydroxy or amino and R" is hydroxy or hydrogen, at least one of R' and R" being hydroxy, or where R' is nitro when R" is hydroxy. In the preferred embodiments of this process aspect, the intermediate substituted-nicotinonitriles where at least one of R' and R" is methoxy undergo several conversions to produce the final products, namely, cleavage of the methoxyphenyl or dimethoxyphenyl ethers to produce the corresponding hydroxyphenyl or dihydroxyphenyl moieties, to hydrolyze the nitrile to the corresponding carboxylic acid and to decarboxylate said acid.

The term "lower-alkyl" as used herein, e.g., as one of the meanings of R and $R_1$, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-hydroxyalkyl", as used herein, e.g., as one of the meanings for $R_1$ in formula I, means a hydroxyalkyl radical having from two to six carbon atoms and having its hydroxy group and its free valence bond (or connecting linkage) on different carbon atoms which can be arranged as straight or branched chains, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxyamyl, 6-hydroxyhexyl, and the like.

The compounds of the invention having formula I or II in which at least one of R' and R" is amino are useful both in the free base and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base form of the cardiotonically active compounds of the invention are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same.

The reaction of 1-$R_1$-1,2-dihydro-2-oxo-5-(3-R'-4-R''-phenyl)-6-R-nicotinonitrile, where $R_1$ and R are defined as in formula II, R' is hydrogen, hydroxy, methoxy or amino and R'' is hydroxy, methoxy or hydrogen, preferably at least one of R' and R'' being methoxy, or where R' is nitro when R'' is hydroxy or methoxy, with 85% phosphoric acid to produce 1-$R_1$-5-(3-R'-4-R''-phenyl)-6-R-2(1H)-pyridinone, where $R_1$ and R have the meanings given above, R' is hydrogen, hydroxy or amino and R'' is hydroxy or hydrogen, at least one of R' and R'' being hydroxy, or where R' is nitro when R'' is hydroxy, is carried out by heating the reactants, preferably refluxing the reaction mixture.

The above intermediate 1-$R_1$-1,2-dihydro-2-oxo-5-(3-R'-4-R''-phenyl)-6-R-nicotinonitrile where $R_1$ is defined as in formula II, R is lower-alkyl, R' is hydrogen, hydroxy, methoxy or amino and R'' is hydroxy, methoxy or hydrogen, or where R' is nitro when R'' is hydroxy or methoxy, is prepared by reacting 1-(3-R'-4-R''-phenyl)-2-(dimethylamino)ethenyl lower-alkyl ketone with N-$R_1$-α-cyanoacetamide. This reaction is carried out preferably by heating the reactants in a suitable solvent in the presence of a basic condensing agent. The reaction is conveniently run using an alkali metal loweralkoxide, preferably sodium methoxide or ethoxide, in dimethylformamide. In practicing the invention, the reaction was carried out in refluxing dimethylformamide using sodium methoxide. Alternatively, methanol and sodium methoxide or ethanol and sodium ethoxide can be used as solvent and basic condensing agent, respectively; however, a longer heating period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like. Alternatively, the intermediate nicotinonitriles compounds where R' and/or R'' represent hydroxy and/or amino can be prepared by first preparing the corresponding compound where R' and/or R'' represent respectively, methoxy and/or nitro, which in turn is then reacted with a reagent capable of converting methoxy to hydroxy and/or with a reagent capable of converting nitro to amino.

The above intermediate 1-(3-R'-4-R''-phenyl)-2-(dimethylamino)ethenyl lower-alkyl ketone is prepared by reacting 3-R'-4-R''-benzyl lower-alkyl ketone with dimethylformamide di-(lower-alkyl) acetal. This reaction is carried out by mixing the reactants neat or in the presence of a suitable solvent The reaction is conveniently run at room temperature, i.e., about 20°–25° C., or by warming the reactants to about 100° C., preferably in an aprotic solvent, preferably dimethylformamide. Other suitable solvents include tetrahydrofuran, acetonitrile, ether, benzene, dioxane, and the like. Alternatively, the reaction can be run using no solvent, using an excess of dimethylformamide di-(lower-alkyl)acetal.

The intermediate 3-R'-4-R''-benzyl lower-alkyl ketones (II) are generally known compounds which are prepared by known methods, e.g., Beilstein 8, 87, 102, 103, 280 (1925); ibid. 14, 59 (1931).

The intermediate 1-$R_1$-1,2-dihydro-2-oxo-5-(3-R'-4-R''-phenyl)-6-R-nicotinonitrile where $R_1$ is defined as in formula II, R is hydrogen, R' is hydrogen, hydroxy, methoxy or amino and R'' is hydroxy, methoxy or hydrogen, is prepared by the generally known procedure of reacting the appropriate 2-(substituted-phenyl)-3-dimethylamino-2-propenal with N-$R_1$-cyanoacetamide, as shown in said Shen et al U.S. Pat. Nos. 3,655,679 and 3,703,582.

The following examples will further illustrate the invention without, however, limiting it thereto.

A.
1-$R_1$-1,2-DIHYDRO-2-OXO-5-(SUBSTITUTED-PHENYL)-6-R-NICOTINONITRILES

A-1. 1,2-Dihydro-5-(4-methoxyphenyl)-2-oxonicotinonitrile—To a stirred mixture containing 13.5 g. of sodium methoxide in 200 ml. of methanol was added 12.61 g. of cyanoacetamide and 20.5 g. of 3-dimethylamino-2-(4-methoxyphenyl)-2-propenal and the resulting mixture was heated with stirring on a steam bath for 12 hours. The reaction mixture was concentrated in vacuo to yield a yellow semi-solid material. This material was suspended in water and the resulting mixture (partial dissolution) was acidified with acetic acid. The separated solid was collected, washed with water, dried in vacuo, recrystallized from dimethylformamide and dried in vacuo for 24 hours at 0.01 mm. and 80° C. to produce 11.6 g. of 1,2-dihydro-5-(4-methoxyphenyl)-2-oxonicotinonitrile, m.p. 294°–295° C. with decomposition.

The intermediate 3-dimethylamino-2-(4-methoxyphenyl)-2-propenal was prepared by the procedure described below in the second paragraph following Example A-11 but using α-(4-methoxyphenyl)acetic acid in place of α-(3,4-dimethoxyphenyl)acetic acid.

A-2. 1,2-Dihydro-5-(4-hydroxyphenyl)-2-oxonicotinonitrile—To a mixture containing 11.3 g. of 1,2-dihydro-5-(4-methoxyphenyl)-2-oxonicotinonitrile in 110 ml. of collidine was added 36.8 g. of anhydrous lithium iodide and the resulting mixture was refluxed with stirring under nitrogen for 24 hours. The reaction mixture was cooled, treated with ice and acidified with 6N hydrochloric acid and cooled. The precipitated solid was collected and dried in vacuo to yield 8.5 g. of 1,2-dihydro-5-(4-hydroxyphenyl)-2-oxonicotinonitrile. The product obtained herein was combined with another sample obtained by comparable run and the combined material was recrystallized from dimethylformamide-methanol and dried at 0.01 mm and 100° C. for 7 days to produce 13.47 g. of 1,2-dihydro-5-(4-hydroxyphenyl)-2-oxonicotinonitrile, m.p. >300° C.

A-3. 1,2-Dihydro-5-(4-nitrophenyl)-2-oxonicotinonitrile, m.p. 339°-346° C. with decomposition, 87.2 g., was obtained following the procedure described in Example A-1 using 83 g. of 3-dimethylamino-2-(4-nitrophenyl)-2-propenal, 50.4 g. of cyanoacetamide, 54 g. of sodium methoxide and 1500 ml. of methanol.

A-4. 5-(4-Aminophenyl)-1,2-dihydro-2-oxonicotinonitrile—A mixture containing 14.47 g. of 1,2-dihydro-5-(4-nitrophenyl)-2-oxonicotinonitrile, 1.0 g. of 10% palladium-on-charcoal, 300 ml. of dimethylformamide and 5.76 g. of (3.9 ml.) of methanesulfonic acid was treated under catalytic hydrogenation conditions until the theoretical quantity of hydrogen to reduce nitro to amino was taken up. The reaction mixture was filtered through diatomaceous earth to remove the catalyst. The filtrate was concentrated in vacuo to a volume of about 200 ml. and to the concentrate was added slowly 3.9 ml. (5.76 g.) of methanesulfonic acid, the mixture stirred for about 10 minutes and then treated with about 500 ml. of methylene dichloride. The crystalline solid was collected, dissolved in about 900 ml. of hot methanol, the hot solution treated with decolorizing charcoal and then filtered through a sintered glass funnel. The filtrate was cooled and the separated crystalline material was collected and recrystallized from methanol. The resulting product was dissolved in 150 ml. of warm 2N hydrochloric acid, the solution basified with aqueous sodium hydroxide solution and cooled. The resulting white solid was collected, dissolved in 400 ml. of methanol, treated with 2 ml. of methanesulfonic acid, the mixture concentrated to remove the solvent and recrystallized twice from methanol, filtering the hot, yellow solution thru a sintered glass funnel and concentrating the filtrate to a volume of about 200 ml., cooling, collecting the solid and drying it in vacuo at 80° C. to yield 6.1 g. of 5-(4-aminophenyl)1,2-dihydro-2-oxonicotinonitrile as its monomethanesulfonate, m.p. 252°-260° C.

A-5. 1,2-Dihydro-5-(4-methoxyphenyl)-6-methyl-2-oxonicotinonitrile—A mixture containing 100 g. of 97% 3-(4-methoxyphenyl)propan-2-one, 94.2 ml. of dimethylformamide dimethyl acetal and 500 ml. of dimethylformamide was stirred at room temperature for over 17 hours and then on a steam bath for 2 hours. There was then added 23.6 ml. of dimethylformamide dimethyl acetal followed by stirring at room temperature for about 75 minutes and then on a steam bath for about 2 and ½ hours. To the partially cooled solution containing 4-dimethylamino-3-(4-methoxyphenyl)-3-buten-2-one was added 79.8 g. of sodium methoxide and 74.5 g. of cyanoacetamide and the resulting mixture was heated on a steam bath with stirring for about 12 hours. The reaction mixture was then diluted with about 1.5 liters of water and the resulting suspension was acidified with acetic acid. The separated solid was collected and recrystallized from dimethylformamidewater to yield 116.8 g. of 1,2-dihydro-5-(4-methoxyphenyl)-6-methyl-2-oxonicotinonitrile, m.p. 253°-255° C. A sample of this material was further purified by recrystallizing successively from methanol and acetic acid-water and drying at 90°-95° C. in vacuo for over 24 hours to yield said product, m.p. 258°-259° C.

A-6. 1,2-Dihydro-5-(4-hydroxyphenyl)-6-methyl-2-oxonicotinonitrile, m.p. 275°-276° C. with decomposition, was prepared following the procedure described in Example A-2 using 12.0 g. of 1,2-dihydro-5-(4-methoxyphenyl)-6-methyl-2-oxonicotinonitrile, 36.8 g. of lithium iodide and 120 ml. of collidine.

Following the procedure described in Example A-1 but using in place of 3-dimethylamino-2-(4-methoxyphenyl)-2-propenal a molar equivalent quantity of the appropriate 3-dimethylamino-2-(substituted-phenyl)-2-propenal, it is contemplated that the corresponding 1,2-dihydro-2-oxo-5-(substituted-phenyl)nicotinonitriles of Examples A-7 through A-11 can be obtained A-7. 1,2-Dihydro-5-(3-methoxyphenyl)-2-oxonicotinonitrile.

A-8. 1,2-Dihydro-5-(3,4-dimethoxyphenyl)-2-oxonicotinonitrile.

A-9. 1,2-Dihydro-5-(3-nitrophenyl)-2-oxonicotinonitrile.

A-10. 1,2-Dihydro-5-(3,4-dinitrophenyl)-2-oxonicotinonitrile.

A-11. 1,2-Dihydro-5-(4-methoxy-3-nitrophenyl)-2-oxonicotinonitrile.

The intermediate 3-dimethylamino-2-(substituted-phenyl)-2-propenals used in Examples A-7 through A-11 are either known or are readily prepared from known compounds by conventional means, e.g., by reacting an α-(substituted-phenyl)-acetic acid with the reaction product obtained by reacting dimethylformamide with a phosphorus oxyhalide, preferably the oxychloride or oxybromide, as illustrated in the following paragraph for the intermediate used to prepare Example A-8.

The intermediate 2-(3,4-dimethoxyphenyl)-3-dimethylamino-2-propenal was prepared as follows: To a chilled 1260 ml. portion of dimethylformamide was added dropwise 230 ml. of phosphorus oxychloride followed by addition of 196 g. of α-(3,4-dimethoxyphenyl)acetic acid. The reaction mixture was heated at about 70° C. on a steam bath for 3 hours, allowed to cool and then concentrated in vacuo to remove the solvent and excess volatile reactants. The resulting product was used directly in the above procedure to prepare Example A-8.

Following the procedure described in Example A-2 or A-4 but using in place of 1,2-dihydro-5-(4-methoxyphenyl or 4-nitrophenyl)-2-oxonicotinonitrile a molar equivalent quantity of the appropriate 1,2-dihydro-5-(substituted-phenyl)-2-oxonicotinonitrile, it is contemplated that the corresponding compounds of Examples A-12 through A-16 can be obtained.

A-12. 1,2-Dihydro-5-(3-hydroxyphenyl)-2-oxonicotinonitrile, m.p. 283°-287° C., using the corresponding 5-(3-methoxyphenyl) compound and the procedure of Example A 2.

A-13. 1,2-Dihydro-5-(3,4-dihydroxyphenyl)-2-oxonicotinonitrile using the corresponding 5-(3,4-dimethoxyphenyl) compound and the procedure of Example A-2.

A-14. 1,2-Dihydro 5-(4-methoxy-3-aminophenyl)-2-oxonicotinonitrile using the corresponding 5-(4-methoxy-3-nitrophenyl) compound and the procedure of Example A-4.

A-15. 1,2-Dihydro-5-(3-aminophenyl)-2-oxonicotinonitrile using the corresponding 5-(3-nitrophenyl) compound and the procedure of Example A-4.

A-16. 1,2-Dihydro-5-(3,4-diaminophenyl)-2-oxonicotinonitrile the corresponding 5-(3,4-dinitrophenyl) compound and using the procedure of Example A-4.

Following the procedure described in Example A-5 but using in place of 3-(4-methoxyphenyl)propan-2-one a molar equivalent quantity of the appropriate 3-(substituted-phenyl)propan-2-one or substituted-benzyl lower-alkyl ketone, it is contemplated that the corresponding 1,2-dihydro-2-oxo-5-(substituted-phenyl)-6-methyl(or lower-alkyl)-nicotinonitriles of Examples A-17 to A-20 can be obtained A-17. 1,2-Dihydro-5-(3-methoxyphenyl)-6-methyl-2-oxonicotinonitrile, m.p. 247°–250° C., starting with 3-(3-methoxyphenyl)propan-2-one.

A-18. 1,2-Dihydro-5-(3,4-dimethoxyphenyl)-6-methyl-2-oxonicotinonitrile, m.p. 262°–263° C., starting with 3-(3,4-dimethoxyphenyl)propan-2-one via 4-dimethylamino-3-(3,4-dimethoxyphenyl)-3-buten-2-one, m.p. 94°–95.5° C. (prepared as in Example A-5).

A-19. 1,2-Dihydro-5-(4-nitrophenyl)-6-methyl-2-oxonicotinonitrile, starting with 3-(4-nitrophenyl)propan-2-one.

A-20. 1,2-Dihydro-5-(4-methoxyphenyl)-6-ethyl-2-oxonicotinonitrile, starting with 1-(4-methoxyphenyl)-butan-2-one.

A-21. 1,2-Dihydro-5-(4-methoxy-3-nitrophenyl)-6-methyl-2-oxonicotinonitrile, m.p. >300° C., starting with 3-(4-methoxy-3-nitrophenyl)propan-2-one. Alternatively, 1,2-dihydro-5-(4-methoxy-3-nitrophenyl)-6-methyl-2-oxonicotinonitrile was prepared by nitrating 1,2-dihydro-5-(4-methoxyphenyl)-6-methyl-2-oxonicotinonitrile by heating it with concentrated nitric acid in acetic acid on a steam bath for two hours and then pouring the reaction mixture into water and collecting the product.

Following the procedure described in Example A-2 or A-4 but using in place of 1,2-dihydro-5-(4-methoxyphenyl or 4-nitrophenyl)-2-oxonicotinonitrile a molar equivalent quantity of the appropriate 1,2-dihydro-5-(substituted-phenyl)-6-(lower-alkyl)-2-oxonicotinonitrile, it is contemplated that the corresponding compounds of Examples A-22 through A-27 can be obtained.

A-22. 1,2-Dihydro-5-(3-hydroxyphenyl)-6-methyl-2-oxonicotinonitrile, using 1,2-dihyro-5-(3-methoxyphenyl)-6-methyl-2-oxonicotinonitrile and the procedure of Example A-2.

A-23. 1,2-Dihydro-5-(3,4-dihydroxyphenyl)-6-methyl-2-oxonicotinonitrile, m.p. 267° C. (chars), using 1,2-dihydro-5-(3,4-dimethoxyphenyl)-6-methyl-2-oxonicotinonitrile and the procedure of Example A-2.

A-24. 1,2-Dihydro-5-(4-aminophenyl)-6-methyl-2-oxonicotinonitrile, using 1,2-dihydro-5-(4-nitrophenyl)-6-methyl-2-oxonicotinonitrile and the procedure of Example A-4.

A-25. 1,2-Dihydro-5-(4-hydroxyphenyl)-6-ethyl-2-oxonicotinonitrile, using 1,2-dihydro-5-(4-methoxyphenyl)-6-ethyl-2-oxonicotinonitrile and the procedure of Example A-2.

A-26. 1,2-Dihydro-5-(4-hydroxy-3-nitrophenyl)-6-methyl-2-oxonicotinonitrile, m.p. 290°–293° C., using 1,2-dihydro-5-(4-methoxy-3-nitrophenyl)-6-methyl-2-oxonicotinonitrile and the procedure of Example A-2.

A-27. 1,2-Dihydro-5-(3-amino-4-hydroxyphenyl)-6-methyl-2-oxonicotinonitrile, m.p. >300° C. as its (1:1) phosphate ($H_3PO_4$) salt, using 1,2-dihydro-5-(4-hydroxy-3-nitrophenyl)-6-methyl-2-oxonicotnonitrile and the procedure of Example A-4 or using 1,2-dihydro-5-(4-methoxy-3-aminophenyl)-6-methyl-2-oxonicotinonitrile and the procedure of Example A-2.

Following the procedure described in Example A-5 but using in place of cyanoacetamide a molar equivalent quantity of the appropriate N-$R_1$-cyanoacetamide, it is contemplated that the corresponding 1-$R_1$-1,2-dihydro5-(4-methoxyphenyl)-6-R-2-oxonicotinonitrile of Examples A-28 and A-29 can be obtained.

A-28. 1,2-Dihydro-5-(4-methoxyphenyl)-1,6-dimethyl-2-oxonicotinonitrile, using N-methylcyanoacetamide.

A-29. 1,2-Dihydro-1-(2-hydroxyethyl)-5-(4-methoxyphenyl)-6-methyl-2-oxonicotinonitrile, using N-(2-hydroxyethyl)cyanoacetamide.

Following the procedure described in Example A-2 but using in place of 1,2-dihydro-5-(4-methoxyphenyl)2-oxonicotinonitrile a molar equivalent quantity of the appropriate 1-$R_1$-1,2-dihydro-5-(4-methoxyphenyl)-6-(lower-alkyl)-2-oxonicotinonitrile, it is contemplated that the corresponding compounds of Examples A-31 and A-32 can be obtained.

A-31. 1,2-Dihydro-5-(4-hydroxyphenyl)-1,6-dimethyl-2-oxonicotinonitrile.

A-32. 1,2-Dihydro-1-(2-hydroxyethyl)-5-(4-hydroxyphenyl)-6-methyl-2-oxonicotinonitrile.

B.
1-$R_1$-5-(SUBSTITUTED-PHENYL)-6-R-2(1H)-PYRIDINONES—

B-1. 5-(4-Hydroxyphenyl)-6-methyl-2(1H)-pyridinone— A mixture containing 20 g. of 1,2-dihydro-5-(4-methoxyphenyl)-6-methyl-2-oxonicotinonitrile and 200 ml. of 85% phosphoric acid was refluxed with stirring for about 15 hours, allowed to cool and then poured onto ice. The aqueous mixture was made alkaline with concentrated ammonium hydroxide and the resulting white precipitate was collected, washed with water and dried in vacuo at 60° C. This material was purified by first recrystallizing it from dimethylformamide-water and then taking up the recrystallized material in about 150 ml. of 10% aqueous sodium hydroxide solution, filtering off a small quantity of undissolved white material and acidifying the filtrate with acetic acid whereupon a white precipitate separated. The precipitate was collected, dried in vacuo at 60° C. to yield 11 g. of 5-(4-hydroxyphenyl)-6-methyl-2(1H)-pyridinone, m.p. 275°–276° C.

5-(4-Hydroxyphenyl)-6-methyl-2(1H)-pyridinone also was produced by following the above procedure of Example B-1 using in place of 1,2-dihydro-5-(4-methoxyphenyl)-6-methyl-2-oxonicotinonitrile a molar equivalent quantity of 1,2-dihydro-5-(4-hydroxyphenyl)-6-methyl-2-oxonicotinonitrile.

B-2. 5-(3-Hydroxyphenyl)-6-methyl-2(1H)-pyridinone, m.p. 285°–288° C., was obtained following the procedure described in example B-1 using 1,2-dihydro-5-(3-methoxyphenyl)-6-methyl-2-oxonicotinonitrile and several recrystallizations of the product from 95% ethanol.

5-(3-Hydroxyphenyl)-6-methyl-2(1H)-pyridinone also is produced by following the above procedure of Example B-2 using in place of 1,2-dihydro-5-(3-methoxyphenyl)-6-methyl-2-oxonicotinonitrile a molar equivalent quantity of 1,2-dihydro-5-(3-hydroxyphenyl)-6-methyl-2-oxonicotinonitrile.

B-3. 5-(4-Hydroxyphenyl)-2(1H)-pyridinone, m.p. >300° C., was prepared following the procedure described in Example B-1 using in place of 1,2-dihydro-5-(4-methoxyphenyl)-6-methyl-2-oxonicotinonitrile a molar equivalent quantity of 1,2-dihydro-5-(4-methoxyphenyl)-2-oxonicotinonitrile.

B-4. 5-(3-Hydroxyphenyl)-2(1H)-pyridinone as its hydrate (4:1), m.p. 246°–248° C. with decomposition, was prepared following the procedure described in Example B-1 using in place of 1,2-dihydro-5-(4-methoxyphenyl)-6-methyl-2-oxonicotinonitrile a molar equivalent quantity of 1,2-dihydro-5-(3-methoxyphenyl)-2-oxonicotinonitrile.

Following the procedure described in Example B-1 but using in place of 1,2-dihydro-5-(4-methoxyphenyl)-6-methyl-2-oxonicotinonitrile a molar equivalent quantity of the appropriate 1,2-dihydro-5-(3-R'-4-R''-phenyl)-6-R-2-oxonicotinonitrile, it is contemplated that there can be obtained the following 5-(3-R'-4-R''-phenyl)-6-R-2-(1H)-pyridinones of Examples B-5 thru B-14.

B-5. 5-(4-Aminophenyl)-2-(1H)-pyridinone from 5-(4-aminopheny)-1,2-dihydro-2-oxonicotinonitrile.

B-6. 5-(3,4-Dihydroxyphenyl)-2(1H)-pyridinone from 1,2-dihydro-5-(3,4-dimethoxyphenyl)-2-oxonicotinonitrile or 1,2-dihydro-5-(3,4-dihydroxyphenyl)-2-oxonicotinonitrile.

B-7. 5-(4-Hydroxy-3-aminophenyl)-2(1H)-pyridinone from 1,2-dihydro-5-(4-methoxy-3-aminophenyl)-2-oxonicotinonitrile or 1,2-dihydro-5-(4-hydroxy-3-aminophenyl)-2-oxonicotinonitrile.

B-8. 5-(3-Aminophenyl)-2(1H)-pyridinone from 1,2-dihydro-5-(3-aminophenyl)-2-oxonicotinonitrile.

B-9. 5-(3,4-Diaminophenyl)-2(1H)-pyridinone from 1,2-dihydro-5-(3,4-diaminophenyl)-2-oxonicotinonitrile.

B-10. 5-(3,4-Dihydroxyphenyl)-6-methyl-2(1H)-pyridinone, m.p. 261°–262° C., from 1,2-dihydro-5-(3,4-dimethoxyphenyl)-6-methyl-2-oxonicotinonitrile or 1,2-dihydro-5-(3,4-dihydroxyphenyl)-6-methyl-2-oxonicotinonitrile.

B-11. 5-(4-Hydroxyphenyl)-6-ethyl-2(1H)-pyridinone from 1,2-dihydro-5-(4-methoxyphenyl)-6-ethyl-2-oxonicotinonitrile or 1,2-dihydro-5-(4-hydroxyphenyl)-6-ethyl-2oxonicotinonitrile.

B-12. 5-(4-Aminophenyl)-6-methyl-2(1H)-pyridinone from 1,2-dihydro-5-(4-aminophenyl)-6-methyl-2-oxonicotinonitrile.

B-13. 5-(4-Hydroxyphenyl)-1,6-dimethyl-2(1H)pyridinone from 1,2-dihydro-5-(4-methoxyphenyl)-1,6-dimethyl-2-oxonicotinonitrile or 1,2-dihydro-5-(4-hydroxyphenyl)-1,6-dimethyl-2 oxonicotinonitrile.

B-14. 1-(2-Hydroxyethyl)-5-(4-hydroxyphenyl)-6-methyl-2(1H)pyridinone from 1,2-dihydro-1-(2-hydroxyethyl)-5-(4-methoxyphenyl)-6-methyl-2-oxonicotinonitrile or 1,2-dihydro-1-(2-hydroxyethyl)-5-(4-hydroxyphenyl)-6-methyl-2-oxonicotinonitrile.

B-15. 5-(4-Hydroxy-3-nitrophenyl)-6-methyl-2(1H)-pyridinone — A mixture containing 2.0 g. of 5-(4-hydroxyphenyl)-6-methyl-2(1H)-pyridinone and 25 ml. of acetic acid was heated with stirring on a steam bath to obtain a solution. To the hot solution, no longer heated on a steam bath, was added dropwise with stirring a solution containing 0.42 ml. of 90% nitric acid in 4.2 ml. of acetic acid. The resulting reaction mixture was allowed to stand for thirty minutes and to it was then added 40 ml of water. The resulting precipitate was collected, washed successively with water and acetone and dried in vacuo at 50° C. to yield 1.41 g. (57% yield) of 5-(4-hydroxy-3-nitrophenyl)-6-methyl-2(1H)-pyridinone, m.p. 260°–262° C.; this material was used directly in Example B-16. In another run, this compound was recrystallized from dimethylformamide, then dissolved in 10% aqueous sodium hydroxide solution, reprecipitated with 6N hydrochloric acid, collected, washed successively with water and acetone and dried in vacuo at 50° C. to produce (78% recovery on recrystallization) 5-(4-hydroxy-3-nitrophenyl)-6-methyl-2(1H)-pyridinone, m.p. 262°–264° C.

B-16. 5-(3-Amino-4-hydroxyphenyl)-6-methyl-2(1H)-pyridinone — A mixture containing 8.8 g. of 5-(4-hydroxy-3-nitrophenyl)-6-methyl-2(1H)-pyridinone, 1200 ml. of ethanol and 0.9 g. of 10% palladium-on-charcoal was shaken with hydrogen under pressure at room temperature under catalytic hydrogenation conditions until tlc analysis showed that the starting material was consumed. The reaction mixture was filtered and the filtrate was evaporated in vacuo to remove the solvent. The residue was dissolved in dimethylformamide and the product was precipitated by addition of ether. The precipitate was collected, washed successively with water and acetone and dried in vacuo at 50° C. to yield 6.2 g. (60% yield) of 5-(3-amino-4-hydroxyphenyl)-6-methyl-2(1H)-pyridinone, m.p. 279°–283° C. This product was placed in 125 ml. of methanol, the mixture acidified with hydrogen chloride in ether and the product precipitated as its hydrochloride salt by addition of ether. The salt was dissolved in water, the solution treated with decolorizing charcoal and filtered. The product in free base form was precipitated by adding 1N aqueous sodium hydroxide solution to the filtrate to neutral pH. The precipitate was collected, washed successively with water and acetone and dried in vacuo at 50° C. to yield 2.3 g. (30%) of 5-(3-amino-4-hydroxyphenyl)-6-methyl-2(1H)-pyridinone, m.p. 282°-283° C.

The utility of the compounds of formulas I and II as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I or II at doses of 3, 10, 30, and/or 100 μg/ml., were found to cause significant increases, that is, greater than 25% (cat) or 30% (g. pig) in papillary muscle force and significant increases, that is, greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. The compounds of formula I, in particular, those where R is methyl, are markedly more active as cardiotonics compared with the corresponding compounds where R is hydrogen. For example, the compound of Example B-1, namely, 5-(4-hydroxyphenyl)-6-methyl-2(1H)-pyridinone, when tested by said cat atria and papillary muscle procedure was found to cause papillary muscle and right atrial force increases of 86% and 77% when tested at 10 μg./ml. compared with corresponding respective papillary muscle and right atrial force increases of 97% and 53% found for prior art 5-(4-hydroxyphenyl)-2(1H)-pyridinone, the compound of Example B-3, when tested by the same procedure at 100 μg./ml., that is, at ten times the dose level. Similarly, the compound of Example B-2, namely, 5-(3-hydroxyphenyl)-6-methyl-2(1H)-pyridinone, when tested by said guinea pig atria and papillary muscle procedure was found to cause papillary muscle and right atrial force increases of 143% and 79% respectively at 10 μg./ml. compared with corresponding increases of 78% and 86% for 5-(3-hydroxyphenyl)-2(1H)-pyridinone, the compound of Example B-4, when tested by the same procedure at 100 μg./ml., that is, at ten times the dose level. Other illustrative guinea pig papillary muscle and right atrial rate increases for compounds of the invention are: 92% and 38% at 10 μg./ml. for Example B-16; 170% and 300% at 30 μg./ml. and 102% and 123% at 10 μg./ml. for Example B-10; and, 139% and 73% at 10 μg./ml. and 65% and 68% at 3 μg/ml for Example B-15.

When tested by said anesthetized dog procedure, the compounds of formulas I and II or pharmaceutically-acceptable acid-addition salts thereof where at least one of R' and R" is amino at doses of 0.3, 1.0, 3.0 and/or 10 mg./kg. administered intravenously were found to cause significant increases, that is, 25% or greater, in cardiac contractile force or cardiac contractility with lower changes in heart rate and blood pressure. For example, when tested at 0.10, 0.3 and/or 1.0 mg./kg. by this procedure the compounds of Examples B-1, B-2 and B-15 were found to cause increases of 50% and greater in contractile force and lower changes in heart rate and blood pressure.

The present invention includes within its scope a cardiotonic composition for increasing cardiac contractility, said composition comprising a pharmaceutically acceptable carrier and, as the active component thereof, a cardiotonically effective amount of the compound of formula I or II. The invention also includes within its scope the method for increasing cardiac contractility in a patient requiring such treatment which comprises administering to such patient said cardiotonic composition providing a cardiotonically effective amount of said compound of formula I or II. In clinical practice said compound will normally be administered orally or parenterally in a wide variety of dosage forms.

Solid compositions for oral admininstration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such a magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueousorganic and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. The process which comprises refluxing a 1-$R_1$-1,2-dihydro-2-oxo-5-(3-R'-4-R''-phenyl)-6-R-nicotinonitrile, where $R_1$ is hydrogen, lower-alkyl or lower-hydroxyalkyl, R is hydrogen or lower-alkyl, R' is hydrogen, hydroxy, methoxy or amino and R'' is hydroxy, methoxy or hydrogen, or where R' is nitro when R'' is hydroxy or methoxy, with a multi-molar excess of 85% phosphoric acid to produce 1-$R_1$-5-(3-R'-4R''-phenyl)-6-R-2(1H)-pyridinone, where $R_1$ and R have the meanings given above, R' is hydrogen, hydroxy or amino and R'' is hydroxy or hydrogen, at least one of R' and R'' being hydroxy, or where R' is nitro when R'' is hydroxy.

2. The process according to claim 1 which comprises refluxing a 1-$R_1$-1,2-dihydro-2-oxo-5-(3-R'-4-R''-phenyl)-6-R-nicotinonitrile, where $R_1$ is hydrogen, lower-alkyl or lower-hydroxyalkyl, R is hydrogen or lower-alkyl, R' is hydrogen, methoxy or amino and R'' is methoxy or hydrogen, at least one of R' AND R'' being methoxy, or where R' is nitro when R'' is methoxy, with a multi-molar excess of 85% phosphoric acid to produce 1-$R_1$-5-(3-R'-4-R''-phenyl)-6-R-2(1H)-pyridinone, where $R_1$ and R have the meanings given above, R' is hydrogen, hydroxy or amino and R'' is hydroxy or hydrogen, at least one of R' and R'' being hydroxy, or where R' is nitro when R'' is hydroxy.

3. The process according to claim 1 using the nicotinonitrile where $R_1$ is hydrogen, R is methyl or ethyl, R' is hydrogen, methoxy or amino and R'' is methoxy or hydrogen, at least one of R' and R'' being methoxy.

4. The process according to claim 3 using 1,2-dihydro-5-(4-methoxyphenyl)-6-methyl-2-oxonicotinonitrile to produce 5-(4-hydroxyphenyl)-6-methyl-2(1H)-pyridinone.

5. The process according to claim 3 using 1,2-dihydro-5-(3methoxyphenyl)-6-methyl-2-oxo-nicotinonitrile to produce 5-(3-hydroxyphenyl)-6-methyl-2(1H)-pyridinone.

6. The process according to claim 3 using 1,2-dihydro-5-(3,4-dimethoxyphenyl)-6-methyl-2-oxo-nicotinonitrile to produce 5-(3,4-dihydroxyphenyl)-6-methyl-2(1H)-pyridinone.

7. The process according to claim 2 using 1,2-dihydro-5-(4-methoxy-3-nitrophenyl)-6-methyl-2-oxonicotinonitrile to produce 5-(4-hydroxy-3-nitrophenyl)-6-methyl-2(1H)-pyridinone.

8. The process according to claim 3 using 5-(3-amino-4-methoxyphenyl)-1,2-dihydro-6-methyl-2-oxonicotinonitrile to produce 5-(3-amino-4-hydroxyphenyl)-6-methyl-2(1H)-pyridinone.

* * * * *